(12) United States Patent
Farina et al.

(10) Patent No.: US 8,476,453 B2
(45) Date of Patent: Jul. 2, 2013

(54) PROCESS FOR THE PREPARATION OF DIMIRACETAM

(75) Inventors: Carlo Farina, Valsolda (IT); Jacopo Roletto, Turin (IT); Stefano Gobbato, Caltignaga (IT)

(73) Assignee: Neurotune AG, Schlieren (CH)

( * ) Notice: Subject to any disclaimer, the term of this patent is extended or adjusted under 35 U.S.C. 154(b) by 0 days.

(21) Appl. No.: 13/811,727

(22) PCT Filed: Jul. 25, 2011

(86) PCT No.: PCT/EP2011/062767
§ 371 (c)(1),
(2), (4) Date: Jan. 23, 2013

(87) PCT Pub. No.: WO2012/013640
PCT Pub. Date: Feb. 2, 2012

(65) Prior Publication Data
US 2013/0123509 A1    May 16, 2013

(30) Foreign Application Priority Data
Jul. 26, 2010    (EP) .................................... 10170741

(51) Int. Cl.
*C07D 487/04*    (2006.01)

(52) U.S. Cl.
USPC ...................................................... 548/302.7

(58) Field of Classification Search
USPC ...................................................... 548/302.7
See application file for complete search history.

(56) References Cited

FOREIGN PATENT DOCUMENTS

| EP | 0 335 483 | 10/1989 |
|---|---|---|
| WO | 93/09120 | 5/1993 |

OTHER PUBLICATIONS

International Search Report issued Sep. 22, 2011 in International (PCT) Application No. PCT/EP2011/062767.
Pinza et al., "Synthesis and Pharmacological Activity of a Series of Dihydro-1*H*-pyrrolo[1,2-a]imidazole-2,5(3 *H*,6 *H*)-diones, a Novel Class of Potent Cognition Enhancers", Journal of Medicinal Chemistry, American Chemical Society, vol. 36, No. 26, 1993, pp. 4214-4220.

*Primary Examiner* — Laura L. Stockton
(74) *Attorney, Agent, or Firm* — Wenderoth, Lind & Ponack, L.L.P.

(57) ABSTRACT

The invention relates to a method of manufacture of dimiracetam (2,5-dioxohexahydro-1 H-pyrrolo[1,2-a]imidazole), characterized in that a 4-oxo-butanoic acid ester is condensed with glycinamide in a one-pot reaction with a controlled pH. The reaction may be performed in aqueous solution or in an anhydrous lower alcohol solution.

14 Claims, No Drawings

PROCESS FOR THE PREPARATION OF DIMIRACETAM

FIELD OF THE INVENTION

The invention relates to a novel manufacturing process for dimiracetam giving this compound in high purity and good yield.

BACKGROUND OF THE INVENTION

WO 93/09120 describes a process for the preparation of dimiracetam (2,5-dioxohexa-hydro-1H-pyrrolo[1,2-a]imidazole) 1 and related compounds. 5-Ethoxy-2-pyrrolidone is reacted with benzyl carbamate with a catalytic amount of p-toluenesulfonic acid to give 5-benzyloxycarbonylamino-2-pyrrolidone. This compound is then deprotonated at the pyrrolidine nitrogen with sodium hydride in acetonitrile, and reacted with ethyl bromoacetate to give ethyl 5-benzyloxycarbonylamino-2-oxo-1-pyrrolidine-acetate 2. Cyclization can then be performed after cleavage of the ethyl ester and/or the benzyloxycarbonyl protecting group in the presence of a variety of cyclizing agents.

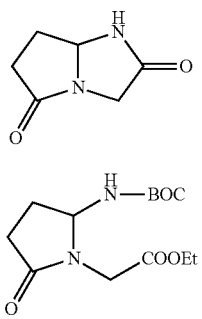

The synthesis and pharmacological activity of dimiracetam are explained in M. Pinza et al., J. Med. Chem. 36:4214-20 (1993). Dimiracetam 1 contains both the 2-pyrrolidinone and 4-imidazolidinone nuclei, already recognized as important for cognition enhancing activity. In addition, this structure maintains the backbone of piracetam (2-oxo-1-pyrrolidinyl-acetic acid amide) and oxiracetam (4-hydroxy-2-oxo-1-pyrrolidinyl-acetic acid amide) with the acetamide side chain restricted in a folded conformation. Its ability to reverse scopolamine-induced amnesia was assessed in a one trial, step-through, passive avoidance paradigm. The main feature observed is a potent antiamnestic activity after i.p. administration. Dimiracetam completely retains activity when given orally, being 10-30 times more potent than the reference drug oxiracetam.

The use of dimiracetam in the treatment of chronic pain is disclosed in WO 2008/125674. At doses higher than reported for cognition enhancing activity, dimiracetam was able to completely revert hyperalgesia or allodynia associated with several models of chronic pain, e.g. in iatrogenic neuropathies associated with antiviral and chemotherapeutic drug treatments and in painful conditions caused by osteoarthritis.

A method of treatment, prevention and/or delay of progression of neuropathic pain is disclosed in US 2010/0125096 based on a new inventive dosage regimen.

In EP 0 335 483 (example 9) and in M. Pinza et al., J. Med. Chem. 36:4214-20 (1993), it is reported that dimiracetam can be obtained by condensation reaction of isobutyl 4-oxobutanoate 3 with glycinamide hydrochloride 4, adjusting the pH to pH 9.5 after the dissolution of glycinamide hydrochloride in water and before the addition of isobutyl 4-oxobutanoate.

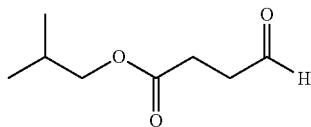

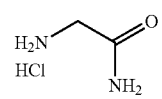

The crude dimiracetam obtained form the synthesis is purified by column chromatography and isolated with an overall yield of 19.1% from glycinamide.

SUMMARY OF THE INVENTION

The invention relates to the synthesis of dimiracetam 1, characterized in that a 4-oxo-butanoic acid ester (I), wherein R is lower alkyl, is condensed with glycinamide (II) or an acid addition salt thereof in a one-pot reaction with a controlled pH. The reaction may be performed in aqueous solution or in an anhydrous lower alcohol solution.

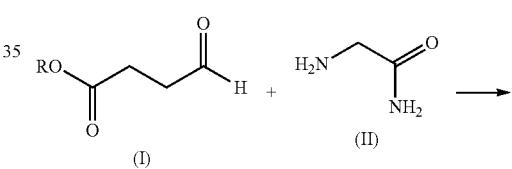

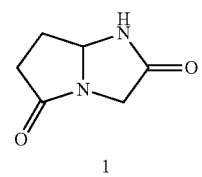

DETAILED DESCRIPTION OF THE INVENTION

The present invention relates to a new efficient process for the synthesis of dimiracetam, characterized in that a 4-oxo-butanoic acid ester (I) is condensed with glycinamide (II) or an acid addition salt thereof in a one-pot reaction with a controlled pH.

In a first particular embodiment of the invention, a 4-oxo-butanoic acid ester (I) is heated with glycinamide (II) or an acid addition salt thereof in aqueous solution, keeping the pH constant during the reaction. In another particular embodiment a 4-oxobutanoic acid ester is condensed with glycinamide or an acid addition salt thereof in an anhydrous lower alcohol, and the intermediate 4-oxo-imidazolidin-2-yl-butanoic acid ester (III) is further treated with a base to give dimiracetam of formula 1.

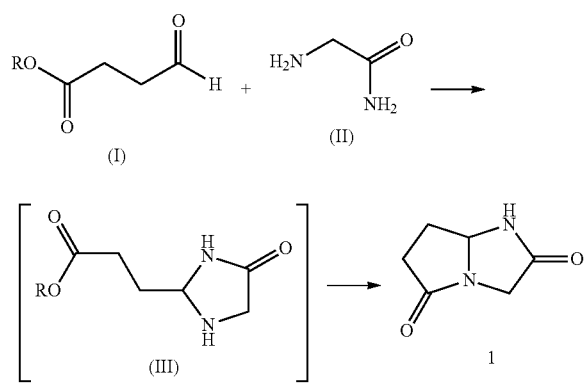

A lower alcohol as understood herein is an alcohol with 1 to 5 carbon atoms, in particular methanol, ethanol, n-propanol, iso-propanol, n-butanol, sec-butanol, iso-butanol, tert-butanol, n-pentanol or iso-pentanol, preferably methanol, ethanol, n-propanol, iso-propanol, n-butanol or sec-butanol, in particular n-propanol.

An ester of 4-oxobutanoic acid is preferably a lower alkyl ester with 1 to 5 carbon atoms, for example the methyl, ethyl, n-propyl, iso-propyl, n-butyl or iso-butyl ester, in particular the methyl or ethyl ester, preferably the ethyl ester.

Glycinamide is preferably provided as an acid addition salt, for example as the hydrochloride or hydrosulfate, in particular the hydrochloride. However, it may also be used as the free base.

As a particular example the 4-oxo-butanoic acid ester is the ethyl ester, ethyl 4-oxo-butanoate of formula 5, and glycinamide is provided as the glycinamide hydrochloride of formula 4. In a particular embodiment of the condensation reaction in aqueous solution the pH is kept within a range of pH 5.5 to 7.5, in particular around 6.6. In another particular embodiment the condensation reaction in aqueous solution is performed at 90 to 100° C. for 0.5 to 10 h, preferably 1 to 3 h, in particular around 1.5 h.

One of the key elements for the one-pot aqueous condensation reaction surprisingly found and very different from the prior art is maintaining a constant and selected pH along the reaction. From a pure technical point of view the constant selected pH is necessary for avoiding a quick degradation of the 4-oxobutanoic acid ester which has an ester moiety easily hydrolizable by water at high pH. The selected value of pH is fundamental for the yield of the one-pot reaction in water because it is the compromise between a basic pH necessary for the formation of the glycinamide base for the reaction with the aldehyde moiety and an acidic pH for decreasing the hydrolysis of the ester moiety of the 4-oxo-butanoic acid ester.

Controlling the pH is best performed with an automated system, which is constantly measuring the pH of the reaction solution and is coupled to a dispenser of an alkaline solution. The alkaline solution may be an aqueous hydroxide solution, for example, a potassium or sodium hydroxide solution, or a carbonate solution, for example potassium or sodium carbonate, preferably sodium carbonate solution, such as 20% $Na_2CO_3$ w/v in water. Whereas it was found that a pH within a range of pH 5.5 to 7.5 is suitable, the best result for the reaction is found when the pH is set to 6.6.

In the prior art the pH control along the reaction was not reported, only at the beginning of the reaction, before addition of aldehyde, the pH was adjusted to pH 9.5. Performing the reaction following the prior art procedure and starting from pH 9.5, ethyl 4-oxobutanoate 5 hydrolyzes and the pH decreases very quickly until reaching a pH lower than pH 5. At this pH the reaction is nearly stopped because the glycinamide is protonated and no longer able to react with the potential remaining aldehyde function.

According to the invention the 4-oxobutanoic acid ester is used in molar excess compared to the amount of glycinamide, for example in an amount of 1 to 3 mol equivalents. The aldehyde function is degraded in the aqueous reaction environment.

The key element for the alternative embodiment wherein the one-pot reaction is conducted in a lower alcohol as solvent and very different from the prior art is the anhydrous condition. Within the selected reaction conditions, the 4-oxobutanoic acid ester (I) is not degraded and hence can react with the glycinamide (II) during the whole reaction time. Whereas a molar excess of 4-oxobutanoate is essential for the reaction in aqueous solution, such an excess is not required for the reaction in anhydrous lower alcohol. pH control is advisable since a constant apparent pH obtained by gradual addition of a suitable base is necessary to regulate the equilibrium of the free base of glycinamide and its protonated form.

In anhydrous conditions the result produced by an automated system keeping the pH constant by adding a base is as important as in aqueous solution. However, in contrast to the aqueous solution, it does not make sense to define a numerical value of a preferred range of pH, since pH measurements are only reliable in aqueous solution. For example, in n-propanol solution an apparent pH of 5.5 was found to be optimal. The skilled person in the art will easily find the appropriate apparent pH value to be used with a corresponding anhydrous lower alcohol solvent. Using the same type of equipment measuring alkalinity and acidity as in aqueous solution, it can then be used to constantly add a base to compensate the formation of acid on progression of the reaction. As an example, a solution of an amine base or of an alkoxide in the particular lower alcohol used as reaction solvent is employed, for example a sodium or potassium alkoxide, such as methoxide, ethoxide or tert-butoxide, sodium hydride, butyllithium, sodium, or sodium or potassium carbonate, in particular potassium tert-butoxide.

In the reaction of the 4-oxobutanoic acid ester (I) with glycinamide (II) or an acid addition salt thereof in anhydrous lower alcohol the intermediate 3-(4-oxoimidazolidin-2-yl)-propanoic acid ester (III) does not spontaneously cyclize to the desired dimiracetam. A suitable base must be added to reach cyclization.

Suitable bases are ammonia, a strong organic amine, for example triethylamine, diisopropylethylamine, pyridine, lutidine, collidine, or 4-N,N-dimethylaminopyridine, an alkoxide, for example tert-butoxide, such as sodium or potassium tert-butoxide or methoxide or ethoxide, an inorganic base, for example solid potassium or sodium carbonate, or ammonium carbonate. Preferred base is ammonia.

In a particular preferred embodiment, the lower alcohol is n-propanol. The molar yield of ethyl 3-(4-oxoimidazolidin-2-yl)propanoate of formula 6 versus glycinamide hydrochloride 4 as determined in the n-propanol reaction mixture is about 80% or more, and the conversion of ethyl 3-(4-oxoimidazolidin-2-yl)propanoate 6 into dimiracetam during the reaction with ammonia is nearly quantitative.

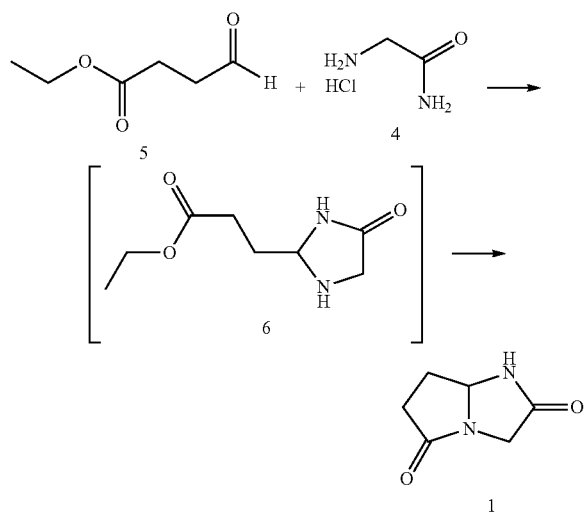

In a particular embodiment, the reaction temperature is between 90 and 120° C., preferably around 100° C., and the reaction time is between 2 and 10 h, preferably around 4 h. After formation of the intermediate of formula (III), e.g. in the form of compound 6, the base is added, e.g. ammonia, and the reaction temperature after addition of ammonia is kept at 30 to 90° C. for 10 to 24 h, in particular at 60 to 70° C. for 16 to 20 h, such as for 18 h.

When the reaction is conducted in a low-boiling alcohol such as methanol, ethanol or iso-propanol, the reaction is preferably conducted in a closed system under pressure in order to reach the desired optimum reaction temperature around 100° C.

The reaction, although called "one-pot", can also be performed using continuous reactor technology.

After the reaction the desired dimiracetam is isolated from the aqueous reaction mixture or the anhydrous lower alcohol reaction mixture by standard procedures, such as extraction, precipitation, filtration and recrystallization. High purity product is obtained by recrystallization from isopropanol.

EXAMPLES

Example 1

Preparation in Aqueous Solution

A solution of 2.56 g (22.7 mmol) of glycinamide hydrochloride (purity 98%) in 200 ml of water is heated to 95° C. and the pH adjusted to 6.6 with $Na_2CO_3$ 20% w/v in water. Then ethyl 4-oxobutanoate (purity 97%) (7.60 g, 56.6 mmol) are added dropwise during four hours maintaining the temperature at 95° C. and the pH at 6.6 by automated addition (pHstat) of $Na_2CO_3$ 20% w/v in water. The solution is stirred at 95° C. for 1.5 hours and then concentrated to a small volume under vacuum. The obtained suspension is treated with 50 ml of isopropanol and the solvent is evaporated at atmospheric pressure. This operation is repeated once again. The residue is diluted with 50 ml of isopropanol and the resulting suspension heated to 60° C. and then filtered. The filtrate is concentrated to about 15 ml, cooled to room temperature and stirring continued for about 2 hours. The white precipitate is collected by suction filtration, washed with 4 ml of isopropanol and dried under vacuum at 60° C. for 12 hours, resulting in 1.8 g of crude dimiracetam (12.8 mmol, 55.5%). Recrystallization from isopropanol (10 volumes) affords 1.6 g (50%) of pure dimiracetam (>99.5% as determined from area % HPLC). Melting point: 154° C.

$^1$H-NMR (in $CD_3OD$): 1.90-2.05 (1H, m), 2.33-2.44 (1H, m), 2.48-2.60 (1H, m), 2.64-2.78 (1H, m), 3.55 and 4.02 (2H, AB q, J=15.9 Hz), 4.76 (s, $H_2O$), 5.34 (1H, t, J=6.12 Hz). $^{13}$C-NMR ($CD_3OD$): 30.8 ($CH_2$), 32.4 ($CH_2$), 47.7 ($CH_2$), 74.0 (CH), 175.2 (C=O), 180.1 (C=O).

FT-IR: 3280 $cm^{-1}$ (NH), 1678-1698 $cm^{-1}$ (C=O), 1222-1284 $cm^{-1}$.

MS: m/z 141 ($MH^+$).

HPLC conditions: Column: Zorbax SB-AQ, 250 mm×4.6 mm×5 mm; detection: UV 200 nm; mobile phase A: water for HPLC grade; mobile phase B: acetonitrile / water (50:50).

Example 2

Preparation in N-Propanol

A suspension of 90.0 g (0.798 mol) of glycinamide hydrochloride (purity 98%) in 7.2 liter of n-propanol is heated to reflux, and 250 ml of solvent are distilled off. A 15% w/v solution of sodium tert-butoxide in n-propanol (260 ml, 0.35 mol) are added and an apparent pH of 5.5 is measured. Maintaining this apparent pH at 5.5 by automatic addition of a 15% w/v solution of sodium tert-butoxide in n-propanol, ethyl 4-oxobutanoate (purity 97%) (262.3 g, 1.955 mol) is added dropwise during four hours while keeping the reaction mixture at reflux, continuously distilling the solvent at about 400 ml/h and continuously adding n-propanol to the reaction mixture at about 400 ml/h. A total amount of 363 ml (0.476 mol) of sodium tert-butoxide 15% w/w solution in n-propanol is added. The mixture is stirred at reflux for additional 1.5 hours and then cooled to 65° C. A 7.5% w/w solution of ammonia in n-propanol (800 g) is slowly added to the mixture during 6 hours, and heating at 65° C. is continued for additional 18 hours. The reaction mixture is cooled to room temperature and the precipitate is filtered off. The clear solution is concentrated to a small volume (about 0.5 liter) under vacuum and stirred at 0° C. for 2 hours. The white precipitate is collected by suction filtration, washed with 50 ml of n-propanol and dried under vacuum at 60° C. for 12 hours to afford pure dimiracetam (65 g, 58.1%), melting at 154° C. HPLC purity: 99.7%

The invention claimed is:

1. A method of manufacturing dimiracetam of formula 1, characterized in that a 4-oxo-butanoic acid ester of formula (I), wherein R is lower alkyl, is condensed with glycinamide of formula (II) or an acid addition salt thereof in a one-pot reaction with a controlled pH wherein the pH is kept within the range of pH 5.5 to 7.5

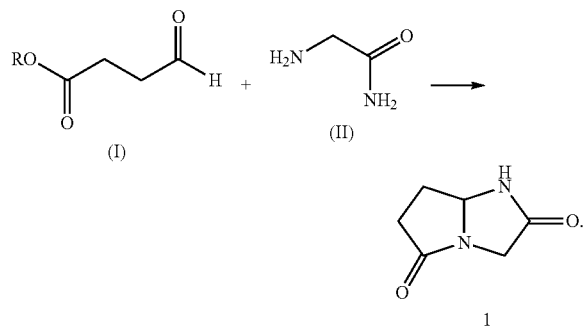

2. The method of claim 1, wherein the 4-oxo-butanoic acid ester (I) is condensed with glycinamide (II) or an acid addition salt thereof in aqueous solution.

3. The method of claim 1, wherein the 4-oxo-butanoic acid ester (I) is condensed with glycinamide (II) or an acid addition salt thereof in anhydrous lower alcohol solution.

4. The method of claim 1, wherein the 4-oxo-butanoic acid ester (I) is ethyl 4-oxobutanoate.

5. The method of claim 1, wherein the glycinamide (II) acid addition salt is glycinamide hydrochloride.

6. The method of claim 2, wherein the reaction temperature is kept at around 100° C. for 0.5 to 10 h.

7. The method of claim 6, wherein the reaction temperature is kept at around 100° C. for 1 to 3 h.

8. The method of claim 2, wherein 1 to 3 molar equivalents of 4-oxobutanoic acid ester (I) are used for one mol equivalent of glycinamide (II).

9. The method of claim 3, wherein the lower alcohol is selected from the group consisting of methanol, ethanol, n-propanol, iso-propanol, n-butanol, sec-butanol, iso-butanol, tert-butanol, n-pentanol and iso-pentanol.

10. The method of claim 9, wherein the lower alcohol is n-propanol.

11. The method of claim 3, wherein ammonia is added in the final step of the reaction.

12. The method of claim 3, wherein the reaction temperature is kept at 90 to 120° C. for 2 to 10 h.

13. The method of claim 11, wherein the reaction temperature after addition of ammonia is kept at 30 to 90° C. for 10 to 24 h.

14. The method of claim 13, wherein the reaction temperature after addition of ammonia is kept at 60 to 70° C. for 16 to 20 h.

* * * * *